(12) United States Patent
Littek et al.

(10) Patent No.: US 6,506,153 B1
(45) Date of Patent: Jan. 14, 2003

(54) METHOD AND APPARATUS FOR SUBJECT MONITORING

(75) Inventors: Amim Littek, Wellington (NZ); Celeste Sabra Littek, Wellington (NZ)

(73) Assignee: Med-Dev Limited (NZ)

( * ) Notice: Subject to any disclaimer, the term of this patent is extended or adjusted under 35 U.S.C. 154(b) by 0 days.

(21) Appl. No.: 09/786,234
(22) PCT Filed: Sep. 1, 1999
(86) PCT No.: PCT/NZ99/00146
§ 371 (c)(1),
(2), (4) Date: Jun. 4, 2001
(87) PCT Pub. No.: WO00/13582
PCT Pub. Date: Mar. 16, 2000

(30) Foreign Application Priority Data

| Sep. 2, 1998 | (NZ) | ................................................. 331697 |
| Jul. 23, 1999 | (WO) | ............................... PCT/NZ99/00112 |

(51) Int. Cl.$^7$ ................................................. A61B 5/00
(52) U.S. Cl. ...................... 600/301; 600/481; 600/483; 600/484; 600/529; 600/534; 600/500; 600/501; 600/502
(58) Field of Search ................................. 600/300, 301, 600/481, 483, 484, 500–502, 529, 534, 595; 297/217.1, 463.2, DIG. 4

(56) References Cited

U.S. PATENT DOCUMENTS

| 4,945,916 | A | * | 8/1990 | Kretschmer et al. ........ 600/484 |
| 4,991,587 | A | * | 2/1991 | Blakely et al. ............. 600/483 |
| 5,448,996 | A | * | 9/1995 | Bellin et al. ................ 600/574 |
| 5,479,932 | A |   | 1/1996 | Higgins et al. |
| 5,853,005 | A | * | 12/1998 | Scanlon ...................... 600/459 |
| 6,002,777 | A | * | 12/1999 | Grasfield et al. ............. 381/67 |

FOREIGN PATENT DOCUMENTS

| EP | 447 024 | 9/1991 |
| EP | 560 351 | 9/1993 |
| EP | 712 604 | 5/1996 |

OTHER PUBLICATIONS

C. Breining et al., "Acoustic echo control: an application of very–high–order adaptive filters," *IEEE Signal Processing Magazine*, pp. 42–69, 1999.

(List continued on next page.)

Primary Examiner—Robert L. Nasser
Assistant Examiner—Patricia Mallari
(74) Attorney, Agent, or Firm—Rothwell, Figg, Ernst & Manbeck

(57) ABSTRACT

A method of monitoring a subject (7) in a vehicle seat (6), the method including: a) acquiring a target signal from the subject with a piezoelectric transducer (1) provided in or on the vehicle seat; b) processing the target signal to extract a cardiac signal (24) and/or a respiratory signal (25); and c) outputting the cardiac and/or respiratory signal. A method of monitoring a subject including: a) acquiring a target signal from the subject; b) bandpass filtering (27) the target signal in accordance with a set of cardiac filter coefficients to extract a cardiac signal (24); c) bandpass filtering (30) the target signal in accordance with a set of respiratory filter coefficients to extract a respiratory signal (25); d) adapting (29, 33) the set of cardiac filter coefficients so as to reduce artefacts in the cardiac signal; e) adapting (50, 32) the set of respiratory filter coefficients so as to reduce artefacts in the respiratory signal; and f) outputting the cardiac and respiratory signal signals.

29 Claims, 5 Drawing Sheets

OTHER PUBLICATIONS

George–Othon Glentis, "Efficient least squares adaptive algorithms for FIR transversal filtering," *IEEE Signal Processing Magazine,* pp. 13–41, 1999.

Patent Abstracts of Japan, C–1153, p. 133 JP 5–261071 A (Matsushita Electric), Oct. 12, 1993.

Patent Abstracts of Japan, C–1147, p. 160 JP 5–245149 A (Matsushita Electric), Sep. 24, 1993.

Derwent Abstract Accession No. 99–012148/02, FR 2 762 984 A (Ecia Equip), Nov. 13, 1998.

Derwent Abstract Accession No. 87–346617/49, SE 452376 B (Nygren), Nov. 23, 1987.

Derwent Abstract Accession No. 93–289848/37, EP 560 351 A (Matsushita Electric), Sep. 15, 1993.

Patent Abstracts of Japan JP 6–205762 A (Matsushita Electric), Jul. 26, 1994.

Patent Abstracts of Japan JP 10–146321 A (Matsushita Electric), Jun. 2, 1998.

Japanese Patent Abstract JP 5–245147 A (Aloka Co Ltd), Sep. 24, 1993.

Japanese Patent Abstract JP 5–245148 A (Matsushita Electric), Sep. 24, 1993.

International Search Report.

* cited by examiner

METHOD AND APPARATUS FOR SUBJECT MONITORING

THE TECHNICAL FIELD

The present invention relates to a method and apparatus for monitoring a subject, for instance in a seat of a land, sea or air based vehicle.

BACKGROUND OF THE INVENTION

It is desirable to be able to monitor the physiological state of a subject in a vehicle seat. One approach is to attach adhesive electrodes to the skin of the subject to acquire a cardiac signal. However this invasive method is cumbersome and not suitable for many applications. It is also desirable to detect the presence or absence of a subject in a vehicle seat. Conventionally this is achieved by installing a crude pressure switch in the vehicle seat. However, such a detector is unable to distinguish between animate and inanimate objects.

A method of extracting cardiac and respiratory signals is used in the infant health monitoring system of U.S. Pat. No. 5,479,932. A signal is acquired from the infant, and the cardiac and respiratory signals are extracted using fixed bandpass filters. A problem with this approach is that the cardiac and respiratory signals may move out of these fixed frequency bands. In addition, there is some overlap in the bandwidth of cardiac and respiratory signals. This results in cardiac signal artefacts in the respiratory signal, and vice versa.

DISCLOSURE OF THE INVENTION

In accordance with the invention there is provided a method of monitoring a human or animal subject comprising:
 a) acquiring a signal from the subject with a transducer;
 b) bandpass filtering the signal in accordance with a set of cardiac filter coefficients to extract a cardiac signal;
 c) bandpass filtering the signal in accordance with a set of respiratory filter coefficients to extract a respiratory signal;
 d) adapting the set of cardiac filter coefficients so as to reduce artefacts in the cardiac signal;
 e) adapting the set of respiratory filter coefficients so as to reduce artefacts in the respiratory signal; and
 f) outputting the cardiac and respiratory signals.

By adaptively filtering both signals, signal artefacts can be reduced. If the signals changed in an uncorrelated way then there would be a problem of overlap between the bandpass regions of the cardiac and respiratory filter coefficients. However, we have recognised that the cardiac and respiratory signals are correlated—ie. heart rate tends to increase and decrease in tandem with respiratory rate. As a result the cardiac and respiratory filter coefficients also tend to increase and decrease in tandem, and thus in general will not overlap.

The coefficients may be adapted by means of a self-adaption feedback loop which identifies and removes periodic signal artefacts. In a preferred example this is implemented by autocorrelating the associated signal, and adapting the set of coefficients in accordance with the autocorrelation signal. Alternatively, or in addition, arfefacts may be removed by means of a cross-adaption feedback loop. In a preferred example this is implemented by subtracting a scaled version of the respiratory signal from the cardiac signal, or vice versa. Both methods (ie. self adaptive and cross-adaptive feedback) enable artefacts associated with the other signal to be at least partially removed, resulting in more accurate cardiac/respiratory signals.

The invention may be employed in a variety of medical or veterinary applications, including monitoring of an animal's vital signs during an operation, or infant apnoea monitoring. Alternatively the method may be employed in a vehicle (ie the subject may be monitored in a vehicle).

The transducer can non-invasively acquire a signal from the subject, even if the subject is wearing heavy clothing as might be required in cold winter climates. By extracting cardiac and respiratory signals it is possible to distinguish between an inanimate object (eg a bag) and a human subject.

The cardiac and respiratory signals may be extracted from separate respective signals acquired using two separate transducers. Preferably the cardiac and respiratory signals are both extracted from a common signal. This enables a single transducer to be used.

When used for in-vehicle monitoring, the output cardiac and/or respiratory signal can be transmitted to a variety of systems associated with the vehicle. At the simplest level the cardiac and/or respiratory signal (or a parameter obtained therefrom, such as breathing rate or heart rate) can be displayed to the subject or another person in the vehicle. Alternatively the signal(s) may simply be stored for later analysis, or transmitted via a wireless link to a remote site for real time analysis, as may be useful in order to analyse the performance of a racing driver or fighter pilot.

In a further alternative the method further comprises analysing the cardiac and/or respiratory signal to obtain a parameter indicative of a physiological state of the subject. For instance an alarm (visual or preferably audible) may be generated if the subject enters a drowsy sleep state (indicated by low cardiac/respiratory rates, or other parameters), or if the subject's cardiac/respiratory rates become abnormal in any other way (eg. high or irregular rates associated with aggressive "road rage" behaviour). Alternatively a control device associated with the vehicle's drive control mechanism (such as a speed limiting mechanism or braking system) may be activated or deactivated when the parameter crosses a predetermined threshold. It is likely that either of these actions will also be enough to wake a sleeping driver.

Alternatively the cardiac and/or respiratory signals may be analysed to determine the presence or absence of a subject in the seat. The seat occupancy determination can then be used to activate or deactivate a variety of systems in the vehicle. For instance if a subject is detected as being present then a visual or audible alarm may be activated, instructing the subject to fasten their seatbelt. Alternatively if no cardiac and/or respiratory signals are present (indicating a lack of seat occupant) then an airbag mechanism may be disabled.

Temperature and/or motor movement signals may also be extracted from the signal so as to provide further information on the subject.

The transducer for acquiring the signal may comprise one or more coaxial cables which utilise a piezoelectric polymer, such as polyvinylidene fluoride (PVDF), as the dielectric material between the centre conductor and the shield. A number of these piezoelectric coaxial cables can be threaded through the padding material of the seat to achieve a matrix of coverage with enough mechanical target detection to allow physical target, cardiac and/or respiratory signals to be reproduced in the coaxial cable, as well as a significant noise input to be extracted. However in a preferred embodiment the transducer comprises a flexible sheet of piezoelectric material. This can cover a wide area of the vehicle seat and thus enables a wide range of sizes of subject to be monitored.

The vehicle may comprise any conveyance for transporting people via land, sea or air. However in a preferred case the vehicle comprises a land based vehicle such as a car, truck etc.

Typically ambient noise is removed by acquiring a noise signal from the subject's environment, acquiring a target signal from the subject, and subtracting the noise signal from the target signal. This is particularly important in the noisy environment usually associated with vehicles. Typically this is achieved using a pair of differentially connected transducers and an instrumentation amplifier.

The invention also extends to apparatus for carrying out the method. Typically the target signal is acquired with a piezoelectric transducer. The signal processing may be carried out in the analog or digital domain. In a preferred example the adaptive bandpass filtering is implemented by a digital signal processor (DSP).

BRIEF DESCRIPTION OF THE DRAWINGS

The invention will now be described by way of example with reference to the accompanying drawings in which.

DETAILED DESCRIPTION OF THE DRAWINGS

Figure 1:
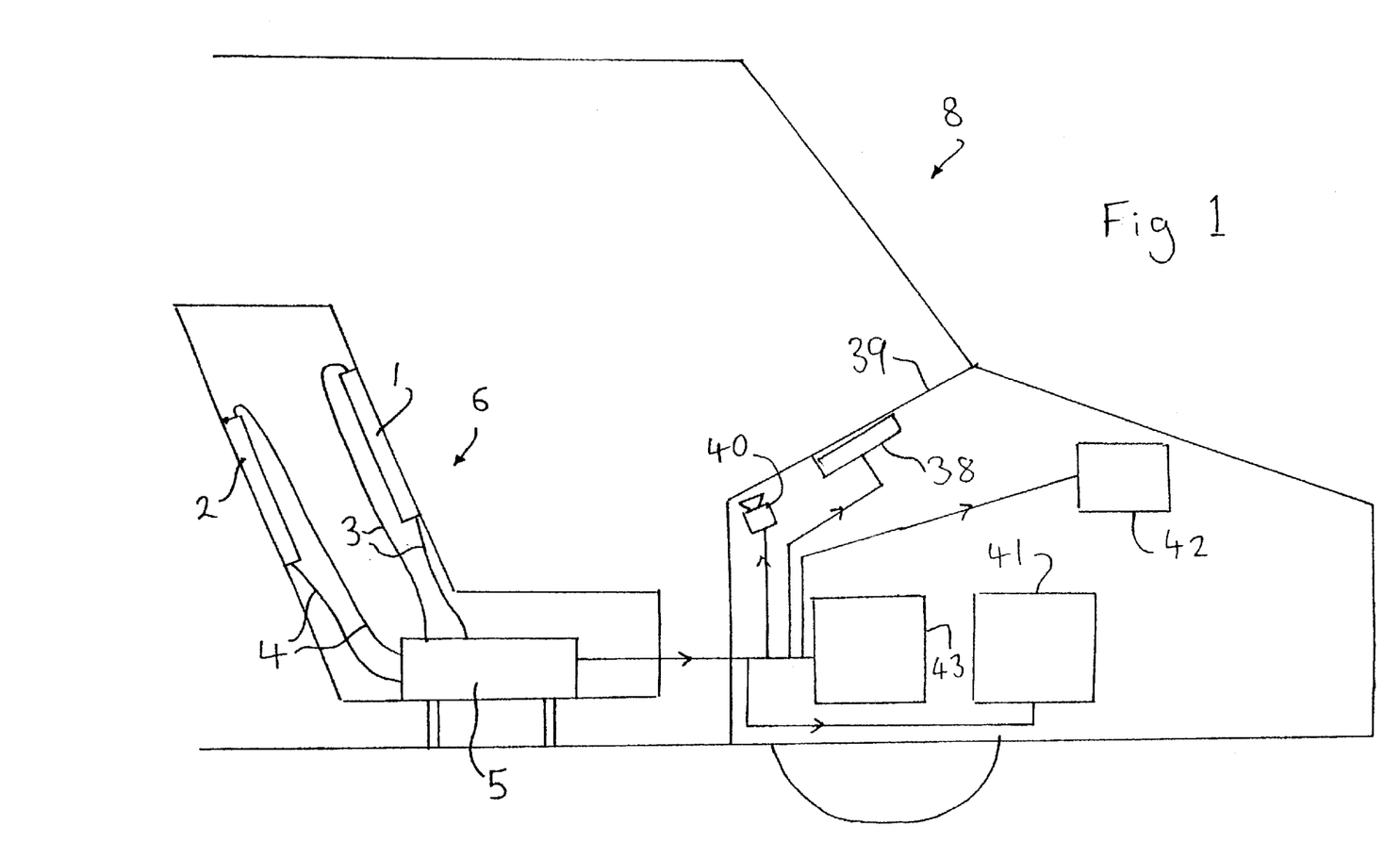
FIG. 1: shows a car incorporating a system for monitoring a subject in a seat of the car.

FIG. 1 shows a representation of a car 8 with a seat 6. A target signal is acquired using a transducer 1 on the front side of the back rest of the seat 6. In an alternative arrangement the transducer 1 may be positioned on the top of the base of the seat. The target signal is transported via wires 3 to signal processing electronics 5. It will be appreciated that the transducer 1 may be removably mounted on the surface of the seat itself, or may be integrated into the construction of the seat as shown. It will also be appreciated that the signal processing electronics 5 need not reside under or within the seat 6. That is, in an alternative construction the target signal is transported directly to main automobile control electronics at another, perhaps more convenient location. Similarly, a reference noise signal is acquired by a transducer 2 positioned on the rear side of the back rest of the seat, and is transported via wires 4 to the signal processing electronics 5.

Figure 2:
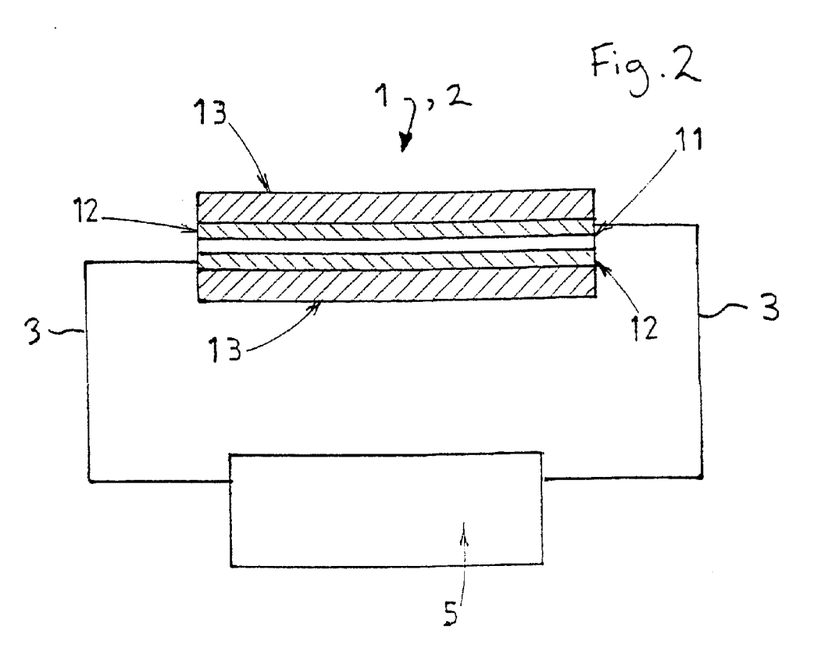
FIG. 2: shows a first example of a suitable transducer.

FIG. 2 shows a first example of the transducers 1,2. The transducer comprises a piezoelectric polymer sheet 11 sandwiched between flexible layers 13. Piezoelectric polymer sheet 11 may be formed of materials and by techniques known in the art. Layer 13 may be an elastomer foam having a density chosen to provide the required deformation of polymer sheet 11 when a desired force is applied to piezoelectric polymer sheet 11.

The wires 3 are connected to electrodes 12, which are either printed or deposited on the polymer sheet 11. The layer 13 is adhered to the sheet by a suitable glue. When sheet 11 is deformed a voltage develops across the sheet 11 related to the force applied to, and hence deformation of, the sheet.

Figure 3:
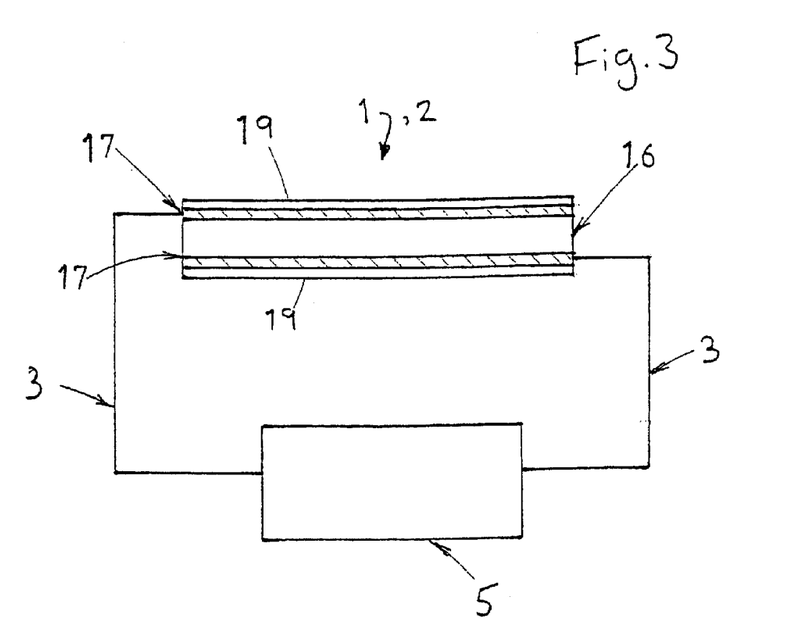
FIG. 3: shows a second example of a suitable transducer

Referring now to FIG. 3 an alternative construction is shown. In this embodiment the transducer is in the form of a piezoelectric polymer foam sheet. A piezoelectric polymer is mixed with an elastomer and foamed to produce a resilient piezoelectric polymer foam sheet 16. Wires 3 are connected to electrodes 17, such as wire or conductive plastic mesh, which are embedded in the foam during the manufacturing process of the piezoelectric polymer foam sheet 16, and detect voltages produced when forces are applied to piezoelectric polymer foam sheet 16, which deform it. The electrodes 17 are coated with non-conductive dielectric layers 19.

Figure 4:
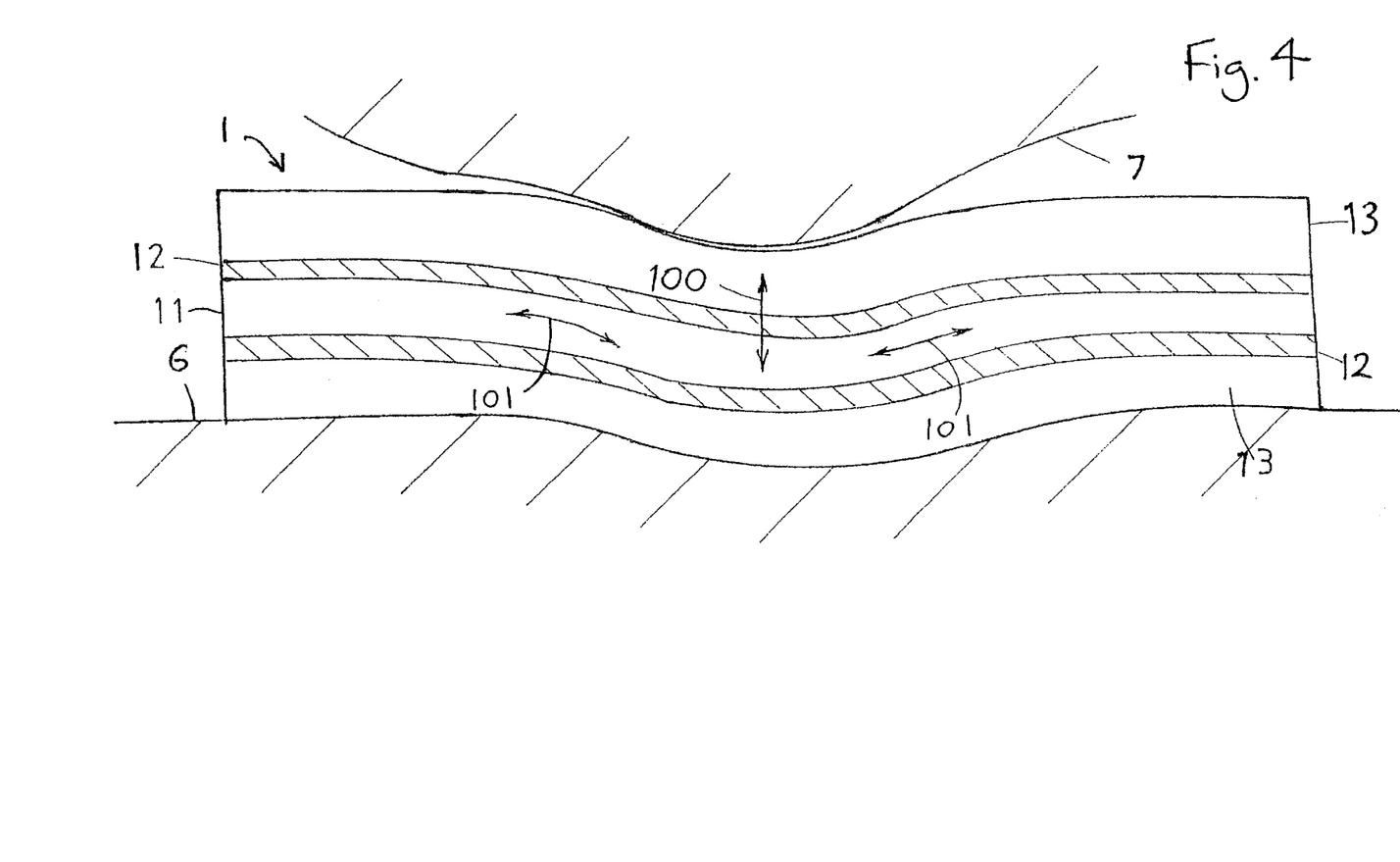
FIG. 4: shows a transducer being deformed.

FIG. 4 illustrates deformation of the transducer. In the example of FIG. 4 the transducer 1 is placed on the vehicle seat 6, but equally the transducer could be integrated into the seat structure behind a layer of padding and thus may not be directly in contact with the seat occupant. The piezoelectric sheet is typically manufactured as a broad (eg square or circular) sheet and it may be cut to size to conform to the size and shape of the seat 6. As the seat occupant 7 moves, the deformation of piezoelectric polymer sheet 11 causes the voltage between electrodes 12 to vary in relation to the changing forces applied to piezoelectric polymer sheet 11. The polymer sheet 11 is also temperature sensitive and generates a signal proportional to temperature.

During manufacture of the piezoelectric polymer sheet 11 the sheet is stretched along its length to pre-align the polymer molecules. The piezoelectric effect is then also enhanced by applying an electric field across the thickness of the sheet as it is cooling down. As a result, the charge generation of the molecules is as much as three orders of magnitude more effective along the length of the sheet (ie. by stretching/releasing along the alignment direction of the molecules) than across the thickness of the sheet.

Movements of the seat occupant cause the sheet 11 to flex and deform across the thickness of the transducer as indicated at 100 in FIG. 4. However by sandwiching the sheet 1 between the foam layers 13, this deformation 100 is converted into a lengthwise deformation indicated at 101. The lengthwise stretching 101 results in a higher voltage output than for the same force without the foam permitting extension. The same lengthwise stretching effect occurs when the transducer of FIG. 3 is used.

The density and thickness of the foam can be selected so as to result in the desired deformation of the transducer to produce the desired range of output voltages. One suitable piezoelectric polymer is PVDF (polyvinylidene fluoride) and its copolymers.

Figure 5:
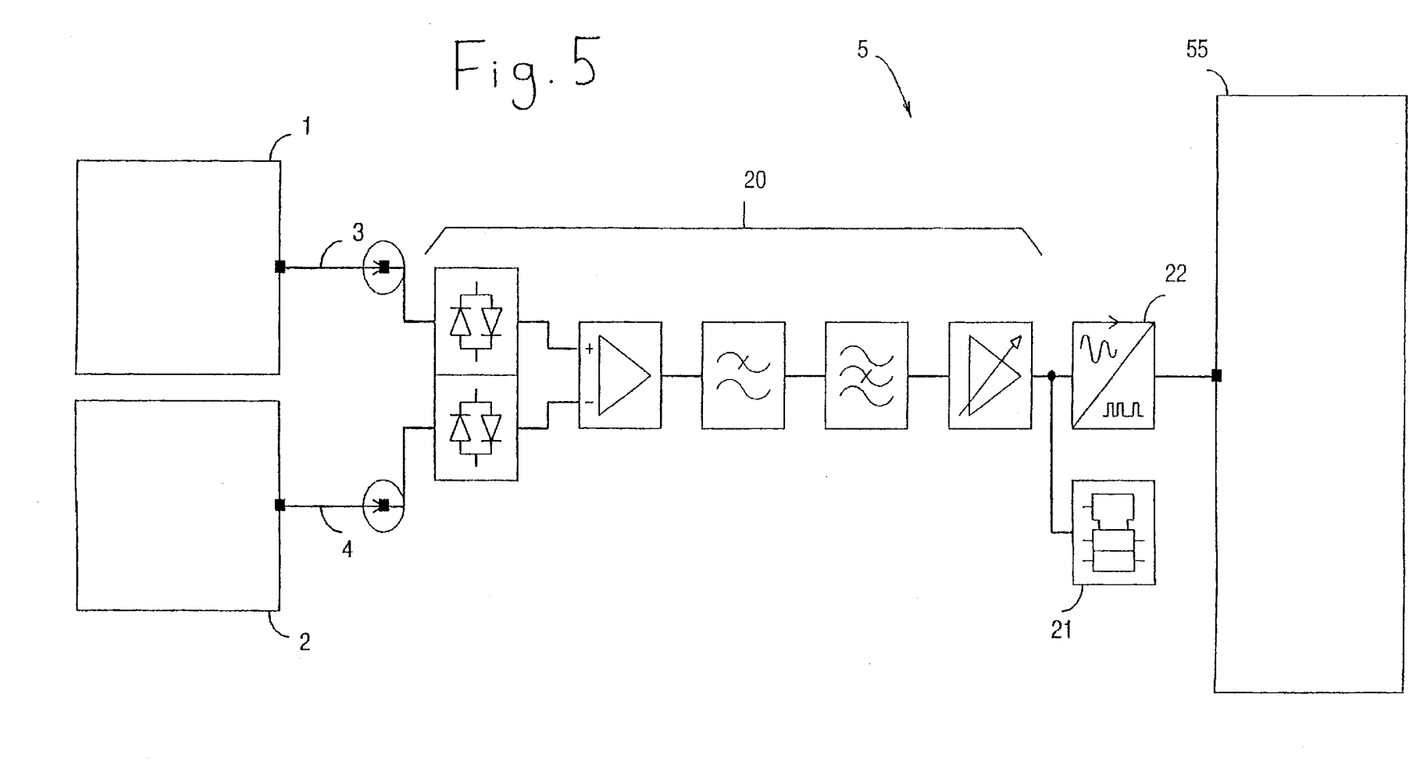
FIG. 5: shows an example of the signal processing electronics.

The signal processing 5 is shown in FIG. 5. The target signal on wires 3 and reference noise signal on wires 4 is first input to signal conditioning 20 which performs a number of tasks in the analog domain, including:

input protection, signal limiting, ground bootstrapping subtraction of the reference noise signal from the target signal using an instrumentation amplifier (instrumentation amplifiers are notably good at common-mode rejection)

coarse low pass filtering (typically with a cutoff frequency between 10 Hz and 30 Hz)

mains or other application-specific notch or comb filtering level translation for the following modules/circuits.

An analog alarm/monitor interface 21 is provided for applications which do not require any digital signal processing. One example of such an application is an infant apnoea monitor which simply monitors the signal level relative to a predetermined threshold.

Figure 6:
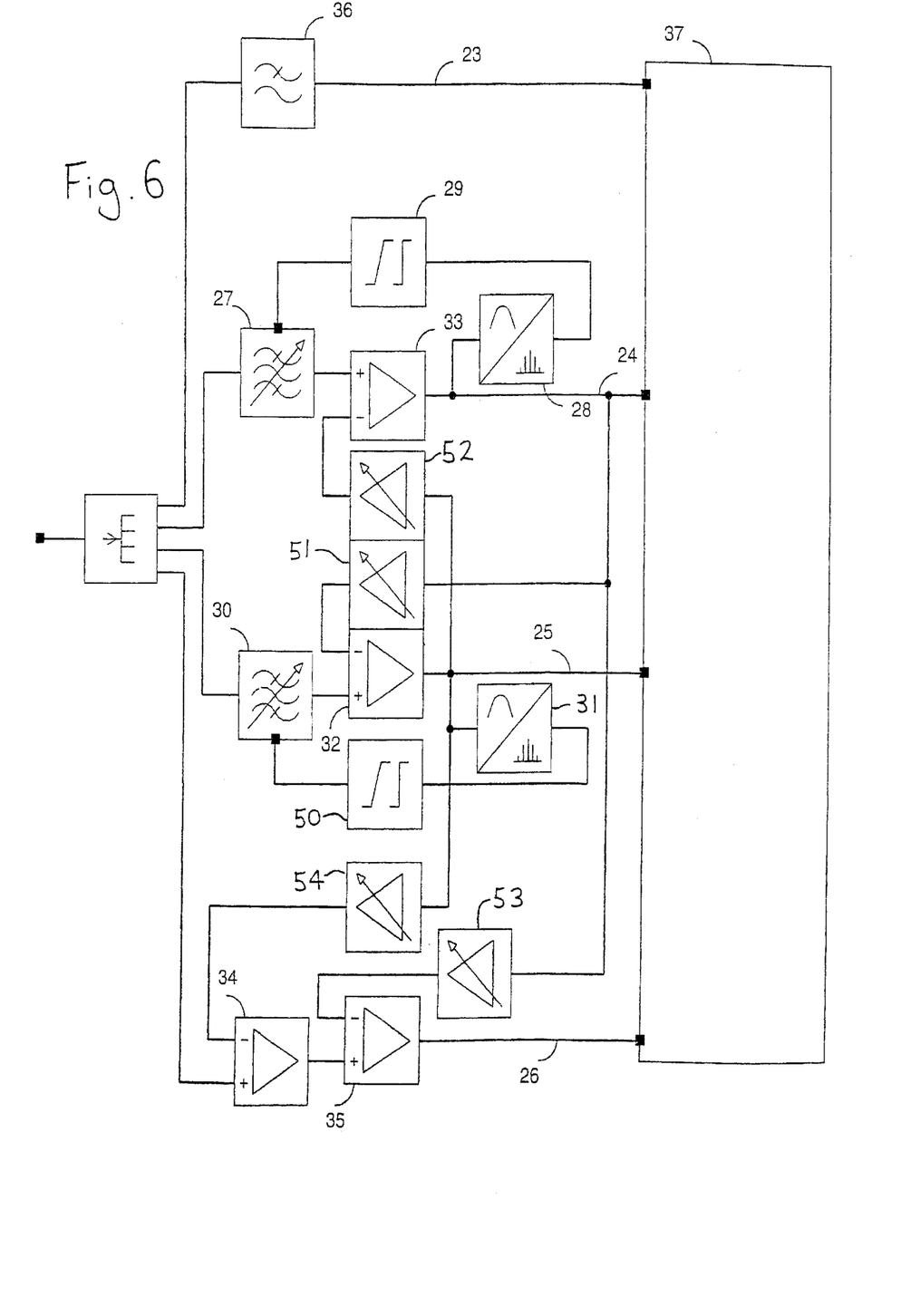
FIG. 6: shows the processing steps implemented by the digital signal processor.

After analog-to-digital conversion at 22 the digital signal is input into a digital signal processor (DSP) 55 which implements the processing method of FIG. 6. The signal processing is split into four parallel signal processing chains for extraction of temperature signals 23, cardiac signals 24, respiratory signals 25 and motor movement signals 26.

The cardiac signal chain comprises an adaptive bandpass filter 27 which filters the digital signal using a set of filter coefficients. Initially the filter coefficients are set so as to filter out signals outside a broad frequency range (eg 1.3 Hz–2.5 Hz) based on the expected frequency range of the cardiac signal. The output of the bandpass filter 27 is then processed by an autocorrelator 28 to generate an autocorrelation signal. A variety of known autocorrelation algorithms may be used. The autocorrelation signal will have peaks at frequencies in the cardiac signal 24 where periodicities are present. If the broad frequency range of the filter is set correctly then the highest peak will be at the fundamental frequency of the cardiac signal (ie the heart rate). There will also be a lower respiration artefact peak at the respiration rate.

The autocorrelation signal is then processed at 29. For instance at 29 the autocorrelation signal may be analysed so as to locate the fundamental cardiac peak (the highest peak). The output of the processor 29 is used by bandpass filter algorithm 27 to adapt the filter coefficients. Initially the range of frequencies will be narrowed from the broad 1.3 Hz–2.5 Hz range in order to filter out unwanted signals (eg the respiration artefacts). Subsequently the frequency range will move up and down as the subject's heart rate varies.

For ease of understanding the autocorrelation, analysing and filtering steps 28,29,27 are illustrated as separate processes in FIG. 6. However it will be understood that these processes will be implemented as an algorithm in the DSP 55.

A wide variety of adaptive filter algorithms may be employed. Examples are given in "Adaptive Filter Theory" by Simon Haykin, ISBN 0-13-322760X, such as Least-Mean-Square algorithms, Recursive-Least-Squares algorithms, Square-Root Kalman filtering, Linear Prediction filtering, Least-Squares lattice filtering etc. Equally, other methods may be used such as neural network (back propagation) algorithms or genetic algorithms (although genetic algorithms may be too slow for some applications).

The respiratory signal path operates along identical principles with an adaptive bandpass filter 30, autocorrelator 31 and self-adaption feedback path analyser 50.

If the heart is beating faster, respiration rate will also tend to increase, and vice versa. Therefore, in general, the adaptive filter coefficients will move up and down in tandem, and will not overlap in most cases.

Even though the self-adaption feedback paths enable cardiac artefacts to be partially removed from the respiratory signal chain, cardiac artefacts will still remain (and similarly respiratory artefacts will remain on the cardiac signal chain). These remaining signal artefacts are removed by the provision of cross-adaption feedback paths between the cardiac and respiratory signal chains.

The cardiac signal 24 is scaled at 51 and subtracted from the respiratory signal by amplifier 32. This cross-adaption process is analogous to the adaptive echo cancellation techniques employed in modems and other communication systems, as discussed in "Gabor Expansion for Adaptive Echo Cancellation", Youhong Lu and Joel M. Morris, IEEE Signal Processing Magazine, March 1999, Vol. 16, No.2, pp 68–80, ISSN 1053-5888.

Similarly the respiratory signal 25 is scaled at 52 and subtracted from the cardiac signal by amplifier 33.

Referring now to the motor movement signal chain, the cardiac and respiratory signals are scaled at 53,54 and subtracted from the motor movement signal 26 by subtracters 35,34. This process is analagous to the cross-adaption feedback used to remove artefacts from the cardiac/respiratory signals. In an alternative method (not shown) the motor movement signal may be extracted by autocorrelating the signal and removing all periodic signal components—this assumes that all motor movement signals will be non-periodic.

Referring now to the temperature signal chain, a temperature signal is extracted by a fixed low pass filter 36. Any changes in temperature will be slow—much slower than the signals in the cardiac, respiratory or motor movement chains. The absolute value of the corner frequency of the low pass filter 36 will be dependent upon the thermal characteristics of the medium in which the transducer is embedded—ie the polyurethane foam of the seat interior, and any exterior cloth/matting. However, typically the corner frequency will be below 0.1 Hz.

The temperature signal may optionally be fed back into the cardiac/respiratory/motor movement signal chains to remove any temperature artefacts.

The four extracted signals are input to control electronics 37 for analysis. The physiological signals may be used in a number of ways.

Referring to FIG. 1, the control electronics 37 drives a display 38 mounted in the dashboard 39 of the car which displays the four signals (or selected ones of the signals) in real time to the vehicle occupants.

The control electronics 37 also analyses the cardiac, respiratory, motor movement and temperature signals to determine whether the seat occupant is becoming drowsy. If the seat occupant is the driver then this requires action to be taken and the control electronics 37 might activate an audible alarm (via loudspeaker 40) or a speed limiter 41 which prevents the car's speed from exceeding a set upper threshold. In an extreme case the control electronics may activate a braking system 42 to stop the car. The braking system 42 may be linked to a conventional automatic navigational aid (not shown) which prevents the car from getting too close to the vehicle in front. A variety of known sleep monitoring algorithms may be employed. Typically these will analyse the heart rate and/or cardiac rate. In addition the algorithms may identify characteristic motor movement patterns or a drop in core temperature which may indicate that the occupant is becoming drowsy.

The cardiac and respiratory signals may also be analysed to determine whether the driver is becoming aggressive or agitated (ie. with a high cardiac/respiration rate) and the systems 40–42 may be activated as appropriate.

In a further alternative the control electronics may simply analyse the four extracted signals to determine the presence or absence of a seat occupant. If an occupant is present the display 38 may be activated to indicate that the occupant should fasten their seatbelt. If the seat 6 is a passenger seat, then the control electronics can enable an airbag system 43 when an occupant is present, and disable the airbag system 43 when no occupant is present.

Where in the foregoing description reference has been made to integers and elements having known equivalents, then such equivalents are incorporated as if individually set forth.

Although this invention has been described by way of example and with reference to possible embodiments thereof, it is to be understood that modifications and improvements may be made without departing from the spirit or scope of the invention.

What is claimed is:

1. A method of monitoring a subject, comprising the steps of:
   a) acquiring a signal from the subject with a transducer;
   b) filtering the signal in accordance with a set of cardiac filter coefficients to extract a cardiac signal;
   c) filtering the signal in accordance with a set of respiratory filter coefficients to extract a respiratory signal;
   d) adapting the set of cardiac filter coefficients so as to reduce artefacts in the cardiac signal;
   e) adapting the set of respiratory filter coefficients so as to reduce artefacts in the respiratory signal;
   f) outputting the cardiac and respiratory signals from respective signal chains; and
   g) reducing signal artefacts by the provision of a cross-adaption feedback path between the cardiac and respiratory signal chains.

2. A method according to claim 1 wherein step d) comprises autocorrelating the cardiac signal to generate a cardiac autocorrelation signal, and adapting the set of cardiac filter coefficients in accordance with the cardiac autocorrelation signal.

3. A method according to claim 1 wherein step e) comprises autocorrelating the respiratory signal to generate a respiratory autocorrelation signal, and adapting the set of respiratory filter coefficients in accordance with the respiratory autocorrelation signal.

4. A method according to claim 1 wherein the cross-adaption feedback path reduces signal artefacts by scaling the cardiac signal to generate a scaled cardiac signal, and subtracting the scaled cardiac signal from the respiratory signal.

5. A method according to claim 1 wherein the cross-adaption feedback path reduces signal artefacts by scaling the respiratory signal to generate a scaled respiratory signal, and subtracting the scaled respiratory signal from the cardiac signal.

6. A method according to claim 1 wherein step a) comprises acquiring a noise signal from the subject's environment, acquiring a target signal from the subject, and generating the signal by subtracting the noise signal from the target signal.

7. A method according to claim 1 wherein the subject is located in a vehicle seat.

8. A method according to claim 1 further comprising displaying the cardiac and/or respiratory signal, or a parameter obtained therefrom.

9. A method according to claim 1 wherein the transducer comprises a flexible sheet of piezoelectric material.

10. A method according to claim 1 further comprising analyzing the cardiac and/or respiratory signal to obtain a parameter indicative of a physiological state of the subject.

11. A method according to claim 10 further comprising generating an alarm when the parameter crosses a predetermined threshold.

12. A method according to claim 10 further comprising activating or deactivating a control device associated with a vehicle's drive control mechanism when the parameter crosses a predetermined threshold.

13. A method according to claim 10 wherein the parameter is indicative of a sleep state of the subject.

14. A method according to claim 10 wherein the parameter comprises respiratory rate or cardiac rate.

15. Apparatus for monitoring a human or animal subject comprising:
   a) a transducer for acquiring a signal from the subject;
   b) a cardiac signal chain including a cardiac adaptive filter for filtering the signal in accordance with a set of cardiac filter coefficients to extract a cardiac signal; means for adapting the set of cardiac filter coefficients so as to reduce artefacts in the cardiac signal; and means for outputting the cardiac signal;
   c) a respiratory signal chain including a respiratory adaptive filter for filtering the signal in accordance with a set of respiratory filter coefficients to extract a respiratory signal; means for adapting the set of respiratory filter coefficients so as to reduce artefacts in the respiratory signal; and means for outputting the respiratory signal; and
   d) a cross-adaption feedback path between the cardiac and respiratory signal chains.

16. Apparatus according to claim 15 wherein the transducer comprises a piezoelectric transducer.

17. Apparatus according to claim 15 comprising means for autocorrelating the cardiac signal to generate a cardiac autocorrelation signal, and means adapting the set of cardiac filter coefficients in accordance with the cardiac autocorrelation signal.

18. Apparatus according to claim 15 comprising means for autocorrelating the respiratory signal to generate a respiratory autocorrelation signal, and means for adapting the set of respiratory filter coefficients in accordance with the respiratory autocorrelation signal.

19. Apparatus according to claim 15 wherein the cross-adaption feedback path comprises means for scaling the cardiac signal to generate a scaled cardiac signal, and means for subtracting the scaled cardiac signal from the respiratory signal.

20. Apparatus according to claim 15 wherein the cross-adaption feedback path comprises means for scaling the respiratory signal to generate a scaled respiratory signal, and means for subtracting the scaled respiratory signal from the cardiac signal.

21. Apparatus according to claim 15 comprising means for acquiring a noise signal from the subject's environment, means for acquiring a target signal from the subject, and means for generating the signal by subtracting the noise signal from the target signal.

22. Apparatus according to claim 15 further comprising means for displaying the cardiac and/or respiratory signal, or a parameter obtained therefrom.

23. Apparatus according to claim 15 wherein the transducer comprises a flexible sheet of piezoelectric material.

24. Apparatus according to claim 15 further comprising means for analyzing the cardiac and/or respiratory signal to obtain a parameter indicative of a physiological state of the subject.

25. Apparatus according to claim 24 further comprising means for generating an alarm when the parameter crosses a predetermined threshold.

26. Apparatus according to claim 24 further comprising means for activating or deactivating a control device associated with a vehicle's drive control mechanism when the parameter crosses a predetermined threshold.

27. Apparatus according to claim 24 wherein the parameter is indicative of a sleep state of the subject.

28. Apparatus according to claim 24 wherein the parameter comprises respiratory rate or cardiac rate.

29. Apparatus for monitoring a subject in a vehicle, the apparatus comprising:

a vehicle seat;

a transducer provided in or on the vehicle seat for acquiring a signal from the subject;

a cardiac signal chain including a cardiac adaptive filter for filtering the signal in accordance with a set of cardiac filter coefficients to extract a cardiac signal; means for adapting the set of cardiac filter coefficients so as to reduce artefacts in the cardiac signal; and means for outputting the cardiac signal;

a respiratory signal chain including a respiratory adaptive filter for filtering the signal in accordance with a set of respiratory filter coefficients to extract a respiratory signal; means for adapting the set of respiratory filter coefficients so as to reduce artefacts in the respiratory signal; and means for outputting the respiratory signal; and a cross-adaption feedback path between the cardiac and respiratory signal chains.

* * * * *